(12) United States Patent
Mulye

(10) Patent No.: US 6,437,000 B1
(45) Date of Patent: Aug. 20, 2002

(54) CONTROLLED RELEASE ORAL DOSAGE FOR SUITABLE FOR ORAL ADMINISTRATION

(75) Inventor: Nirmal Mulye, Long Beach, NY (US)

(73) Assignee: Norstrum Pharmaceuticals, Inc., Long Beach, NY (US)

( * ) Notice: Subject to any disclaimer, the term of this patent is extended or adjusted under 35 U.S.C. 154(b) by 0 days.

(21) Appl. No.: 09/650,837

(22) Filed: Aug. 30, 2000

Related U.S. Application Data

(60) Provisional application No. 60/152,114, filed on Sep. 2, 1999.

(51) Int. Cl.⁷ ............................................. A61K 31/135
(52) U.S. Cl. ...................... 514/647; 514/646; 514/964; 514/970
(58) Field of Search ................................. 514/964, 970, 514/646, 647

(56) References Cited

U.S. PATENT DOCUMENTS

| | | |
|---|---|---|
| 3,488,418 A | 1/1970 | Holliday et al. |
| 3,584,114 A | 6/1971 | Cavalli et al. |
| 3,773,920 A | 11/1973 | Nakamoto et al. |
| 4,025,613 A | 5/1977 | Guy et al. |
| 4,218,433 A | 8/1980 | Kooichi et al. |
| 4,361,545 A | 11/1982 | Powell et al. |
| 4,415,547 A | 11/1983 | Yu et al. |
| 4,539,198 A | 9/1985 | Powell et al. |
| 4,690,822 A | 9/1987 | Uemura et al. |
| 4,690,824 A | 9/1987 | Powell et al. |
| 4,695,467 A | 9/1987 | Uemura et al. |
| 4,748,023 A | 5/1988 | Tamás et al. |
| 4,760,094 A | 7/1988 | Blank et al. |
| 4,767,789 A | 8/1988 | Blank et al. |
| 4,832,957 A | 5/1989 | Dempski et al. |
| 4,880,830 A | 11/1989 | Rhodes |
| 4,900,557 A | 2/1990 | Dell et al. |
| 4,933,182 A | 6/1990 | Higashi et al. |
| 4,938,967 A | 7/1990 | Newton et al. |
| 4,983,399 A | 1/1991 | Maish |
| 4,990,335 A | 2/1991 | Bateman et al. |
| 5,002,774 A | 3/1991 | Agrawala et al. |
| 5,009,897 A | 4/1991 | Brinker et al. |
| 5,128,142 A | 7/1992 | Mulligan et al. |
| 5,164,193 A | 11/1992 | Okada et al. |
| 5,186,943 A | 2/1993 | Okada et al. |
| 5,271,946 A | 12/1993 | Hettche |
| 5,424,075 A | 6/1995 | Daher et al. |
| 5,456,920 A | 10/1995 | Matoba et al. |
| 5,681,581 A | 10/1997 | Dunn |
| 5,719,197 A | 2/1998 | Kanios et al. |
| 6,068,859 A | 5/2000 | Curatolo et al. |

OTHER PUBLICATIONS

Thesis of Nirmal Muyle, *Dicalcium Phosphate Dihydrate Matrices For Sustained Release Of Highly Water Soluble Drugs: Formulation And Kinetics Of Release*, Jan. 1993.

Muyle, N., et al., "Use of Dicalcim Phosphate Dihydrate for Sustained Release of Highly Water Soluble", *Drug Development and Industrial Pharmacy*, vol. 20(17): 2621–2632 (1994).

Muyle, N., et al., "Matrix Type Tablet Formulation For Controlled Release of Highly Water Soluble Drugs", *Drug Development and Industrial Pharmacy*, vol. 20(17): 2633–2643 (1994).

*Primary Examiner*—Alton Pryor
(74) *Attorney, Agent, or Firm*—Scully, Scott, Murphy & Presser

(57) ABSTRACT

The present invention is directed to a pharmaceutical composition, preferably in the form of a tablet comprising a therapeutically effective amount of a medicament in a carrier comprising a water insoluble polymer and a water-insoluble inorganic salt.

38 Claims, No Drawings

CONTROLLED RELEASE ORAL DOSAGE FOR SUITABLE FOR ORAL ADMINISTRATION

RELATED APPLICATION

The present application is claiming benefit of provisional application U.S. Ser. No. 60/152,114, filed Sep. 2, 1999.

FIELD OF THE INVENTION

The present invention relates to a formulation of a water insoluble controlled release carrier to provide controlled release of medicaments.

BACKGROUND OF THE INVENTION

Sustained or slow release compositions containing pharmaceutical medicaments or other active ingredients are designed to contain higher concentrations of the medicament and are prepared in such a manner as to effect sustained or slow release into the gastro-intestinal digestive tract of humans or animals over an extended period of time. Well absorbed oral sustained or slow release therapeutic drug dosage forms have inherent advantages over conventional, immediate release dosage forms. The advantages include less frequent dosing of a medicament and resultant patient regime compliance, a more sustained drug blood level response, therapeutic action with less ingested drug and the mitigation of side effects. By providing a slow and steady release of the medicament over time, absorbed drug concentration spikes are mitigated or eliminated by effecting a smoother and more sustained blood level response.

For this purpose, a controlled release formulation has to meet some criteria; namely it must effect an uniform and constant dissolution of the drugs and it must be effective for an extended period of time. It is also important that such a formulation be simple to make, that the manufacturing process be reproducible and that the product produced by the manufacturing process be uniform. Moreover, if different drugs are used as the active component in the sustained released formulation, it is important that the manufacturing process be easily adaptable to accommodate these various drugs.

To prepare sustained release formulations in the form of a solid oral dosage, such as tablets, various hydrophilic as well as hydrophobic polymers have been utilized. Materials such as waxes have also been used. Formulations made using many of these materials not only offer different release characteristics, but also have several disadvantages associated therewith. For example, the wax matrices are unstable towards heat which can cause sudden release of the drug from the dosage form. On the other hand, the hydrophilic matrices provide sustained release by forming a gel as a protective barrier, which has proven to be an effective method for controlling drug release. However, the swelling of hydrophilic polymers is often affected by the ionic environment of the gastrointestinal tract, which may affect the release rate. Sometimes failure of the matrix has also been observed. Because the hydrophilic matrices swell and erode over a period of time, they can not provide a constant surface area for the release of the drug and in some cases, where the solubility thereof in water is high and the concentration of the drug in the dosage form is very high, they fail to offer controlled release over a long period of time. Thus, there is a need to find a system which does not suffer from these disadvantages.

Various methods such as solvent evaporation, heat melting, direct compression as well as wet granulation have been used to prepare sustained release pharmaceuticals. The only methods which are practical for industrial manufacture of such matrices are direct compression and wet granulation.

Various hydrophobic polymers have been used for fabrication of controlled release matrices. These polymers are elastic and often have poor flow characteristics, thus making them quite unsuitable for commercial manufacture. It is also necessary that the polymer particles coalesce to form an insoluble matrix in order to control the release of the active agent; very high concentrations are often needed. Wet granulation using solutions of such polymers in organic solvents tends to be difficult because solutions containing high polymer content tend to be viscous; therefore to achieve an effective amount of polymer concentration, large amounts of organic solvent are needed. However, many organic solvents are toxic and are quite volatile and flammable, thereby exposing the chemist or other persons directly involved in the manufacture thereof to health and safety hazards. Moreover, multiple granulation procedures are often required.

Aqueous dispersions of such polymers have also been used for wet granulation. Once again multiple granulations are needed to obtain effective amounts of the polymer in the tablet. Unfortunately, high polymer concentration also creates difficulties in granulation by forming rubbery masses.

Mulye, et al. in *Drug Development and Industrial Pharmacy*, 20(17), 2621–2632 (1994) disclose a matrix formulation in the form of a tablet comprising a highly water soluble drug, i.e., chlorpheniramine maleate ("CPM"), bromopheniramine maleate, dextromethorphan•HBr, procaine•HCl, diphenhydramine•HCl, theophylline and niacinamide. These tablets contained, in addition, dicalcium phosphate dihydrate (DCPD) or Eudragit and optionally magnesium stearate. This publication discloses that Eudragit is virtually ineffective in controlling the release profile. It also showed that DCPD was more effective than the Eudragit in controlling the release of the water soluble drug, such as CPM, but that the DCPD containing matrix had a major limitation; when the drug concentration was greater than 5% by weight, the tablet disintegrated.

Mulye, et al., in *Drug Development and Industrial Pharmacy*, 20(17), 2633–2643 (1994) continued the study described hereinabove. In this paper, Mulye, et al. prepared a tablet containing CPM, DCPD and Eudragit. Their study showed that the addition of Eudragit did not affect the drug release profile relative to that obtained with CPM and DCPD in the absence of Eudragit. It was postulated that the hydrophobic polymer had difficulty binding with the hydrophilic surface of the drug, and it was thus ineffective in reducing the release rate. However, when a plasticizer, such as diethylphthalate was added, there was a significant decrease in release rate. These study showed that a plasticizer was required to be present with the DCPD to release the drug in a controlled manner.

However, the present inventor searched for a system wherein a plasticizer was not a necessary component. The present inventor has found such a system.

The present inventor has also overcome the inadequacies of the prior art and is able to prepare a tablet containing the drug and DCPD wherein the drug is present in a concentration greater than 5% by weight. More specifically, he has found a means of preparing a formulation matrix comprising the drug, the hydrophobic salt and a hydrophobic polymer in which the drug is present in greater than 5% by weight.

The present inventor has found that by utilizing a water insoluble inorganic salt in combination with a water insoluble polymer in a ratio within a certain range in the carrier system of the sustained release formulation, the formulation does not suffer from the disadvantages described hereinabove.

SUMMARY OF THE INVENTION

The present invention is directed to a pharmaceutical composition comprising a therapeutically effective amount of a medicament and a controlled release carrier, such carrier comprising a water insoluble polymer and a water insoluble inorganic salt, both being present in a sufficient amount to interact with the drug and form a water insoluble barrier thereover sufficient to retard the release of the medicament in aqueous medium, e.g., the gut, said polymer being present from about 1% up to about 50% by weight of the carrier and said inorganic salt being present from about 1% up to about 95% by weight of the carrier, wherein said carrier is present in an amount ranging from about 1% to about 95% by weight of the composition, and said medicament is present in greater than 5% by weight of the composition.

DETAILED DESCRIPTION OF THE INVENTION

The present invention utilizes a combination of a water insoluble inorganic salt and a hydrophobic polymer to provide a controlled release pharmaceutical composition whereby the active ingredient or medicament is present in amounts greater than 5% by weight.

The controlled release formulation of the present invention is to be administered to mammals in need of such treatment wherein the medicament present in the formulation is administered in effective amounts. By mammals it is meant a vertebrae of the class Mammalia, that is characterized by possession of hair and mammary glands. Examples include, inter alia, dog, cat, horse, pig, goat, cow, and human beings. The preferred species of mammal to which the sustain release formulation of the present invention is to be administered is man.

The dosage form is prepared by conventional techniques, such as by using wet granulation techniques employing either an organic solvent as a granulating medium when the polymer is used in powder form or an aqueous dispersion of the polymer. This procedure offers a one step granulation procedure using minimal, and often no organic solvents, thereby reducing the exposure of the chemist thereto. This formulation technique also permits the use of significantly low concentrations of the polymer.

Thus the invention relates to a pharmaceutical formulation of a water insoluble matrix comprising an inorganic salt and a hydrophobic polymer, said matrix essentially maintaining its integrity and shape while the drug is being released. The dosage form is comprised of a medicament and a controlled release carrier comprising a water insoluble polymer and an inorganic salt in the amounts described hereinabove. The present inventor has found that the inorganic salt when used in conjunction with the water insoluble polymer in the above concentrations facilitates the formation of the pharmaceutical composition and helps maintain its integrity and stability, even when the drug is present in concentrations higher than 5% by weight. Heretofore, as described hereinabove, dicalcium phosphate dihydrate matrices alone, without the insoluble polymer, could not maintain drug integrity at drug concentrations of higher than 5% by weight; when the drug was present in concentrations greater than 5% by weight, the compositions fell apart. However, the present inventor has found that the combination of the water-insoluble organic salt and water insoluble hydrophobic polymer in the amounts described herein permits the formation of the drug formulation and stabilizes the drug formulation, even at drug concentrations greater than 5% by weight. Furthermore, the inventor found that even if the drug is highly water soluble, such as chlorpheniramine maleate, the addition of such polymers did not significantly retard the release of the drug, as did dicalcium phosphate dihydrate in the absence of such polymer, even when the concentration of the drug was less than 5% by weight. Moreover, the inventor has found that the combination in the ratios provided permits the drug to be released in a controlled release manner in an amount more effective than when dicalcium phosphate dihydrate is used alone.

The first component of the pharmaceutical composition of the present invention is the water insoluble polymer. By water insoluble, it is meant that the polymer is substantially or completely water insoluble at 25° C. It is preferred that the polymer has a solubility in water of less than about 0.001 g/l at 25° C. The polymer is preferably an organic polymer. Suitable water insoluble polymers are those that are pharmaceutically safe and non-toxic. Examples include methyl methacrylate polymer (EUDRAGIT), ethyl cellulose, cellulose acetate, polyvinyl acetate, polyvinyl chloride, polystyrene, and the like. The preferred polymer is methyl methacrylate copolymer.

The first component is present in the carrier in amounts ranging from about 1% to about 50% (w/w). It is preferred that the water insoluble polymer is present in at least 1% of the carrier up to about 20% (w/w) of the carrier. It is also preferred that it is present from about 1% up to about 20% and more preferably from about 1% to about 15% by weight of the pharmaceutical composition, it is even more preferred that it is present in about 3% to about 15% (w/w) and most preferably from about 4% to about 10% (w/w) of the pharmaceutical composition. Moreover, it is preferred that the weight ratio of drug to polymer is greater than about 3:1 and more preferably greater than about 5:1. It is preferred that the weight ratio ranges from about 5:1 to about 20:1 and more preferably from about 6:1 to about 15:1.

The second component of the present invention is a pharmaceutically acceptable water insoluble inorganic salt. Again, it is preferred that the solubility of the inorganic salt in water at 25° C. is less than about 0.001 g/l. Moreover, the inorganic salt is non-toxic and pharmaceutically safe.

It is preferred that the inorganic salt is a salt of a calcium salt, magnesium salt, or zinc salt. Examples of inorganic salts suitable for the present invention are dicalcium phosphate, calcium sulfate, tricalcium phosphate, calcium carbonate, magnesium carbonate, zinc carbonate and the like. The more preferred inorganic salt is a calcium salt. The even more preferred inorganic salts are sulfate and especially phosphate salts of calcium. The most preferred inorganic salts are tricalcium phosphate, and especially dicalcium phosphate.

The inorganic salt is present from about 1% to about 95% by weight of the carrier. It is preferred that it is present in at least 50% by weight of the carrier. It is more preferred that it is present in at least 1% and preferably from about 1% to about 94% by weight of the pharmaceutical composition. It is more preferred that the inorganic salt is present in amounts ranging from about 3% to about 60% by weight of the pharmaceutical composition and even more preferably from about 5 to about 40% by weight of the pharmaceutical composition and most preferably from about 10% to about 20% by weight of the pharmaceutical composition.

Without wishing to be bound, it is believed that the inorganic salt interacts with the water insoluble polymer to form a water insoluble barrier by coating the medicament partially or completely, thereby retarding the release of the drug. To be effective, however, the drug must be present in a certain minimal level. In the present invention, the drug is present in amounts greater than at least 5% by weight. Therefore, the inorganic salt and the water insoluble polymer are present in effective amounts relative to the concentration of drug (at least 5%), i.e., both the water insoluble polymer and the inorganic salt are present in amounts effective to retard the release of the drug especially in aqueous media, e.g., in the gastrointestinal tract. As indicated hereinabove, they are present in amounts effective to form a partial or complete barrier or coating around the drug to retard the release of the drug. It is preferred that the inorganic salt is present in amounts by weight equal to or greater than the insoluble polymer. In a more preferred embodiment, it is preferred that the weight ratio of inorganic salt to polymer is at least about 1:1 and more preferably is greater than about 2.5 to 1. In an embodiment, the weight ratio is greater than about 6:1 and more preferably greater than about 9:1. It is more preferred that the weight ratio ranges from about 1:1 to about 100:1 and more preferably from about 1:1 to about 20:1 and most preferably from about 1:1 to about 15:1.

It is also preferred that the weight ratio of drug to inorganic salt is greater than about 0.5 and more preferably greater than about 0.25. It is preferred that the weight ratio ranges from about 0.1 to about 10 and more preferably from about 0.25 to about 10. Furthermore, it is also preferred that the weight ratio of drug to water insoluble polymer is in the weight ratios given hereinabove. Moreover, in the more preferred embodiments, the weight ratios of drug to water insoluble polymer and the drug to water insoluble inorganic salt are both within the ranges indicated. In the most preferred embodiment, these two ratios are within the ranges indicated and also the weight ratio of water insoluble inorganic salt to water insoluble polymer is within the range indicated hereinabove.

The active ingredient can be of any type of medication which acts locally in the mouth or acts systemically, which in the case of the latter, can be administered orally, to transmit the active medicament into the gastrointestinal tract and into the blood, fluids and tissues of the body.

Representative active medicaments include antacids, anti-inflammatory substances, coronary vasodilators, cerebral vasodilators, peripheral vasodilators, anti-infectives, psychotropics, antimanics, stimulants, anti-histamines, laxatives, decongestants, vitamins, gastro-intestinal sedatives, antidarrheal preparations, anti-anginal drugs, vasodilators, antiarrythmics, anti-hypertensive drugs, vasoconstrictors drugs used for migraine treatments, anticoagulants and antithrombotic drugs, analgesics, anti-pyretics, hypnotics, sedatives, anti-emetics, anti-nauseants, anticonvulsants, neuromuscular drugs, hyper- and hypoglycemic agents, thyroid and antithyroid preparations, diuretics, antipasmodics, uterine relaxants, mineral and nutritional additives, antiobesity drugs, anabolic drugs, erythropoietic drugs, antiasthmatics, expectorants, cough suppressants, mucolytics, antiuricemic drugs and other drugs or substances acting locally in the mouth, such as topical anagetics, local anaesthetics, etc.

Typical active ingredients include gastro-intestinal sedatives such as metoclopramide and propantheline bromide; antacids such as aluminium trisilicate, aluminium hydroxide and cimetidine; anti-inflammatory drugs such as phenylbutazone, indomethacin, naproxen, ibuprofen, flurbiprofen, diclofenac, dexamethasone, predinisone and prednisolone; coronary vasodilator drugs such as glyceryl trinitrate, isosorbide dinitrate and pentaerythritil tetranitrate; peripheral and cerebral vasodilators such as soloctidilum, vincamine, naftidorofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic drugs such as flurazepam, diazepam, temazepam, amitryptyline, doxepin, lithium carbonate, lithium sulfate, chlorpromazine, thioridazine, trifluperazine, fluphenazine, piperothiazine, haloperidol, maprotilline hydrochloride, imipramine and desmethylimipramine; central nervous stimulants such as methylphenidate, ephedrine, epinephrine, isoproterenol, amphetamine sulfate and amphetamine hydrochloride; antihistamic drugs such as diphenhydramine, diphenylpyraline, chlorpheniramine and brompheniramine; anti-diarrheal drugs such as bisacodyl and magnesium hydroxide; the laxative drug, dioctyl sodium sulfoxuccinate; nutritional supplements such as ascorbic acid, alpha tocopherol, thiamine and pyridoxine; anti-spasmodic drugs such as dicyclomine and diphenoxylate; drugs affecting the rhythm of the heart, such as verapamil, nifedipine, diltiazem, procainamide, disopyramide, bretylium toxylate, quinidine sulfate and quinidine gluconate; drugs used in the treatment of hypertension such as propranolol hydrochloride, guanethidine mono-sulphate, methyldopa, oxprenolol hydrochloride, captopril and hydralazine; drugs used in the treatment of migraine such as ergotamine; drugs affecting coagulability of blood suchas epsilon aminocaproic acid and protamine sulfate; anagesic drugs such as acetylsalicyclic acid, acetaminophen, codeine phosphate, codeine sulfate, oxydodone, dihydrocodeine tartrate, oxycodeinone, morphine, heroin, nalbuphine, butorphanol tartrate, pentazocine hydrochloride, cyclazacine, pethidine, buprenorphine, scopolamine and mefanamic acid; anti-epileptic drugs such as phenytoin sodium and sodium valproate; neuromuscular drugs such as dantrolene sodium; substances used in the treatment of diabetes such as tolbutamide, disbenase glucagon and insulin; drugs used in the treatment of thyroid gland dysfunction such as triodothyronine, thyroxine and propylthiouracil; diuretic drugs such as furosemide, chlorthalidone, hydrochlorthiazide, spironolactone and trimterene; the uterine relaxant drug ritodrine; appetite suppressants such as fenfluramine hydrochloride, phentermine and diethylproprion hydrochloride; anti-asthmatic and bronchodilator drugs such as aminophyline, theophyline, salbutamol, orciprenaline sulphate and terbutaline sulphate; expectorant drugs such as fuaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; anti-nauseant drugs such as promethazine theoclate; haemopoietic drugs such as ferrous sulphate, folic acid and calcium gluconate; uricosuric drugs such as sulphinpyrazone, allopurinol and probenecid.

Vitamins include such vitamins as vitamin A, vitamin D, vitamin B (d-α-tocopherol acetate, etc.), vitamin $B_1$ (dibenzoylthiamine, fursultiamine hydrochloride, etc.), vitamin $B_1$ (dibenzoylthiamin, fursultiamine hydrochloride, etc.), vitamin $B_2$ (riboflavin butyrate, etc.), vitamin $B_6$ (pyridoxine hydrochloride, etc.), vitamin C (ascorbic acid, sodium L-ascorbate, etc.), vitamin $B_{12}$ (hydroxocobalamin acetate, etc.); minerals such as calcium, megnesium, and iron.

In addition, the drug may be a pharmaceutically acceptable salt of any of the active ingredients enumerated hereinabove.

A lubricant may additionally be and is preferably present in the pharmaceutical formulations of the present invention especially when in the form of a tablet. "Lubricant", as used herein, refers to a material which can reduce the friction between the die walls and the punch faces which occurs during the compression and ejection of a tablet. The lubricant prevents sticking of the tablet material to the punch faces and the die walls. As used herein, the term "lubricant" includes anti-adherents.

Tablet sticking during formation and/or ejection may pose serious production problems such as reduced efficiency, irregularly formed tablets and non-uniform distribution of the medicament in the formulation. To avoid this problem, the present invention contemplates utilizing a lubricating effective amount of the lubricant. Preferably, the lubricant is present in amounts ranging from about 0.1% to about 5% by weight and more preferably from about .5% to about 2% by weight of the pharmaceutical composition, e.g., tablet. Examples of lubricants include stearate salts, e.g., alkaline earth and transition metal salts, such as calcium, magnesium and zinc stearates; stearic acid; polyethylene oxide; talc; hydrogenated vegetable oil; and vegetable oil derivatives, and the like. In addition, the pharmaceutical composition, e.g., tablet, may contain a combination of more than one type of lubricant. Other lubricants that also can be used include silica, silicones, high molecular weight polyalkylene glycol, e.g., high molecular weight polyethylene glycol, monoesters of propylene glycol, and saturated fatty acids containing about 8–22 carbon atoms and preferably 16–20 carbon atoms. The preferred lubricants are the stearate salts, especially magnesium and calcium stearate and stearic acid.

Excipients, such as plasticizers, for example, diethylphthalate (DEP), dibutyl sebacate, triethyl citrate, triacetin, vegetable and mineral oils, polyethylene glycol, and the like, may optionally be present. They enhance tableting characteristics and modify the release of the drug in the gastrointestinal tract when administered to the mammal, and they are present in amounts effective to modify the release in the gastrointestinal tract. The present inventor has noted that, in some cases, the combination of the water-insoluble salt and the water insoluble polymer caused the rate of release of the drug to be slower than desired. In such cases, an excipient, e.g., plasticizer, filler or the like is added to increase the rate of release of the drug. Thus, in one embodiment, a plasticizer may be present in amounts effective to increase the rate of release. Preferably, the plasticizer, when present, is present in the pharmaceutical formulations of the present invention in amounts ranging from about 0.01% to about 25%, and more preferably from about 0.1% to about 10% and most preferably from about 1% to about 5% by weight of the carrier.

Fillers, such as maltodextrin, sugar, lactose, and microcrystalline cellulose may also be present. They are preferably present in amounts ranging from about 2% to about 70% by weight of the carrier, and more preferably from about 10% to about 50% of the carrier and most preferably from about 20% to about 40% by weight of the carrier.

One of ordinary skill in the art understands that excipients, e.g., fillers or plasticizers, have several functions in the pharmaceutical composition. For example, they may be added to enhance tableting characteristics or increase the bulk of the pharmaceutical composition. It is within the purview of one of ordinary skill in the art to determine how much excipient is to be added and the objective that he wishes to accomplishing by adding the same. The amounts given hereinabove for the plasticizer and the fillers are to be understood as preferred embodiment.

Other optional ingredients that are also typically used in pharmaceuticals may also be present, such as coloring agents, preservatives (e.g., methyl parabens), artificial sweeteners, flavorants, anti-oxidants, and the like. Artificial sweeteners include, but are not limited to, saccharin sodium, aspartame, dipotassium glycyrrhizinate, stevia, thaumatin and the like. Flavorants include, but are not limited to, lemon, lime, orange and menthol. The colorants include, but are not limited to, various food colors, e.g., FD&C colors, such as FD&C Yellow No. 6, FD&C Red No. 2, FD&C Blue No. 2, food lakes and the like. Examples of anti-oxidants include ascorbic acid, sodium metabisulphite and the like. These optional ingredients, if present, preferably are present in amounts ranging from about 0.1% to about 5% by weight of the tablet and most preferably less than about 3% (w/w) of the tablet.

The formulations of the present invention are preferably uncoated, but may be coated if desired with one of the many readily available coating systems. However, the combination of the water insoluble polymer and the salt is present in the carrier, and the combination is not present in the coating.

Coating the pharmaceutical composition of the present invention in a unit dosage form, e.g., tablets, serves to mask the taste of the pharmaceutical composition of the present invention. It also makes the unit dosage form of the pharmaceutical composition of the present invention, e.g., tablet, easier to swallow and, in some cases, improves the appearance of the dosage form. The pharmaceutical compositions, e.g., tablet, can be sugar coated and are coated according to the procedures well known in the art. Alternatively, the unit dosage forms of the pharmaceutical composition of the present invention, e.g., tablets, can be coated with any one of numerous polymeric film coating agents frequently employed by formulation chemists. Representative examples of such film coating agents include hydroxypropyl methylcellulose, carboxymethylcellulose, hydroxypropylcellulose, methyl cellulose, ethyl cellulose, acrylic resins, providone, polyvinyl diethylaminoacetate, cellulose acetate phthalate, polyvinyl acetate phthalate, acrylic latex emulsions, ethyl cellulose latex emulsions, and the like. If the coating material is present, it is present in less than about 5% by weight of the tablet, and more preferably about 2–3% w/w.

A procedure for preparing the formulation of the present invention is by the wet granulation process in which all of the components, i.e., medicament, inorganic salt, polymer, and any additional excipient and other optional ingredient (s), except the lubricant, are mixed with a sufficient amount of a granulating solvent to form a substantially uniform blend in a suitable blender, such as a planetary mixer. The granulating vehicle is one that is inert to the components and has a low boiling point, i.e., preferably less than about 120° C. It is preferably a solvent such as an alcohol containing 1–4 carbon atoms, e.g., isopropyl alcohol or ethanol or water or acetone and the like. An aqueous dispersion can also be utilized, especially if the polymeric sustained release material is a methyl methacrylate copolymer, as described above. In a preferred embodiment, the type of granulating vehicle used is dependent upon the identity of the sustained release polymer. It is preferred that when the sustained release material is a copolymer of methyl methacrylate or ethyl acrylate, the granulating vehicle is an alcohol such as isopropyl alcohol or an aqueous latex dispersion of said copolymer.

The substantially uniformly blended mixture may next optionally be milled, e.g., passed through a screen, sieve, etc. to reduce the size of the particles thereof. The screen or sieve, and the like is preferably less than about 140 mesh, and more preferably less than about 100 mesh, and even more preferably, less than about 40 mesh, and most preferably less than about 25 mesh.

Next, the blend is dried. In this step, the solvent is removed from the blend by physical means known to the skilled artisan, e.g., by evaporation or filtration. The resulting granules are again milled, e.g., passed through a screen or sieve to further reduce the size of the particles to the desired size. Then the lubricant is added, and the granules are mixed to provide a uniform and homogenous blend, and then the resulting mixture is compressed to form a tablet. In a preferred variation, the blend can be simultaneously granulated in the granulation vehicle and dried, such as by using a fluid bed granulation process.

When the mixture is homogeneous with respect to the drug, a unit dosage form of the mixture is prepared. The following procedure describes the preparation of a tablet, but once the mixture is homogenous, it can be used to prepare any suitable dosage form used in the pharmaceutical arts by conventional methods. The methodology for preparing a tablet containing the pharmaceutical composition of the present invention is exemplary and it is to be understood that the present invention should not be so limited.

In preparing a tablet, the homogenous mixture is compressed into a tablet form using a tablet machine typically utilized in the pharmaceutical arts. More specifically, the mixture is fed to the die of a tablet press and sufficient pressure is applied to form a solid tablet. Such pressure can vary, and typically ranges from about 1,000 psi to about 6,000 psi and preferably about 2,000 psi force.

After the tablet is formed, the tablet is coated with materials normally used in pharmaceuticals, if desired. If coated, the coating is prepared by techniques known in the art.

As a result of the process described herein, a tablet product is obtained which has the desired hardness and friability typically found for pharmaceutical tablets. The hardness is preferably 5–25 Kp and more preferably 8–20 Kp. In addition, the tablet has an excellent drug release profile. More specifically, it has a predetermined controlled and sustained action and a regular delayed pattern so that the drug is available over a period of up to 36 hours or longer, depending upon the precise tablet size, the identity of the active ingredient, hardness and the particular carrier composition and the needs of the patient. Furthermore, the release profile of each formulation is substantially uniform. Finally, the tablets prepared in accordance with the present invention are hard and dense, have low friability and provide controlled and sustained release over an extended period.

Besides a tablet, the uniformly blended mixture of active ingredient, water insoluble polymer, water insoluble inorganic salt, and any other additional components, can be made into a pellet, capsule, granule, pill or a dragee using conventional techniques known in the art.

The term unit dosage form as employed herein refers to physically discrete units suitable as unitary dosages to human subjects and other mammals, each unit containing a predetermined quantity of medicament calculated to produce the desired effect, in association with the other ingredients of the formulation disclosed herein.

In the formulations described hereinabove, the percent of the components are calculated on a dry weight basis, without reference to any water or other components present.

Unless indicated to the contrary, all percentages are weight percentages relative to the tablet.

Moreover, the terms "drug" and "medicament" are used interchangeable. Furthermore, the terms "sustained release" and "controlled release" are being used interchangeably.

As used herein, the singular shall refer to the plural and vice versa.

The following non-limiting examples further illustrate the present invention.

EXAMPLE 1

Two formulations containing Ferrous Sulfphate as the active ingredient were prepared as follows:

|  | Formulation I | Formulation II |
|---|---|---|
| Dried Ferrous Sulphate | 181 mg | 181 mg |
| Eudragit RSPO | 15 mg | 15 mg |
| Emcompress (dicalcium phosphate dihydrate) | 98 mg | 40 mg |
| Maltodextrin | — | 60 mg |
| Magnesium Stearate | 3 mg | 3 mg |
| Cabosil (fumed silica) | 3 mg | 3 mg |

These were mixed in a wet formulation as follows:

Dried ferrous sulfate, Eudragit RSPO, Dicalcium phosphate dihydrate, and maltodextrin were mixed in a suitable planetary mixer, and the granulating solvent (isopropyl alcohol) was added slowly while mixing. After sufficient solvent was added to form loose agglomerates of the blend, the blend was dried in an oven at 50° C. (usually one hour). The resulting dried blend was then passed through a #20 mesh screen. The lubricants, Magnesium stearate and Cabosil, were added to the dried blend and mixed for 5 minutes. The lubricated blend was compressed into tablets.

The release rate was tested used USP apparatus II at 100 rpm as follows:

Dissolution medium: Distilled water

Temperature: 37.5° C.

Volume: 900 ml.

The time release of these formulations in water was as follows:

| Time (hr) | 1 | 2 | 3 | 4 |
|---|---|---|---|---|
| Formulation I |  |  |  |  |
| % Released | 34 | 48 | 58 | 68 |
| Formulation II |  |  |  |  |
| % Released | 48 | 64 | 75 | 85 |

EXAMPLE 2

The following formulation was prepared using Na Diclofenac as the active ingredient.

| Ingredient | mg/tablet |
|---|---|
| Diclofenac Na | 100 |
| Eudragit RSPN (5%) (methyl methacrylate copolymer) | 15 |
| Dibutyl Phthalate (2%) | 6 |
| Dicalcium phosphate dihydrate | 176 |
| Magnesium Stearate (1%) | 3 |
| Isopropyl alcohol* | q.s. |
| Tablet weight | 300 mg |

*Isopropyl alcohol is not present in final product.

Manufacturing Procedure

The above formulation was prepared in accordance with the procedure of Example 1.

Diclofenac Na, Eudragit RSPM, and Dicalcium phosphate were mixed in a planetary blender until homogenous. Dibutyl phthalate (DBP) was mixed with isopropyl alcohol until homogenous, and this was added to the blend slowly while mixing to form loose agglomerates of the blend. The blend was next dried in an oven (usually about an hour). The resulting dried blend was then passed through a Number 20 mesh screen. The lubricant, magnesium stearate, was added to the dried blend and mixed therewith for five minutes. The lubricated blend was compressed into tablets.

The above formulation is designated Formulation #1. Other formulations (#2–8) were also prepared as described above, except that they varied either in the amount of or identity of plasticizer used or both and/or in the amount of Eudragit utilized. These various formulations are tabulated below:

| Formulation | Polymer by weight | Plasticizer by weight |
| --- | --- | --- |
| 1 | Eudragit RSPM 5% | Dibutyl Phthalate 2% |
| 2 | Eudragit RSPM 5% | Dibutyl Phthalate 0.5% |
| 4 | Eudragit RSPM 3.5% | Dibutyl Phthalate 1% |
| 5 | Eudragit RSPM 5% | Diethyl Phthalate 1% |
| 6 | Eudragit RSPM 5% | Diethyl Phthalate 0.5% |
| 7 | Eudragit RSPM 5% | No Diethyl Phthalate |
| 8 | Eudragit RSPM 5% | Maltodextrin: dicalcium phosphate (50:50) |

All the formulations described in the table hereinabove contained Diclofenac Na 100 mg, Dicalcium phosphate dihydrate, Magnesium Stearate 1% in the amounts indicated, and all were granulated using isopropyl alcohol as described hereinabove. The amount of the polymer and the identity and/or amount of the plasticizer is as indicated hereinabove.

The release rate was tested using a USP apparatus II at 1000 rpm under the following conditions:

Dissolution medium: USP buffer, pH 7.5.

Temperature: 37.5° C.

Volume: 900 mL.

The time release profile of these formulations were as follows:

| Time | Formula 1 | Formula 2 | Formula 3 | Formula 4 | Formula 5 | Formula 6 | Formula 7 | Formula 8 |
| --- | --- | --- | --- | --- | --- | --- | --- | --- |
| 1 | 22 | 18 | 26 | 27 | 21 | 19 | 18 | 27 |
| 2 | 44 | 29 | 49 | 51 | 37 | 32 | 29 | 37 |
| 3 | 60 | 36 | 65 | 68 | 49 | 43 | 38 | 45 |
| 4 | 71 | 42 | 76 | 79 | 60 | 52 | 44 | 52 |
| 5 | 79 | 48 | 82 | 87 | 66 | 59 | 50 | 57 |
| 6 | 86 | 53 | 87 | 92 | 72 | 63 | 54 | 61 |
| 7 | 91 | | | | 77 | 68 | 57 | 65 |
| 8 | | | | | | 72 | | 69 |
| 9 | | | | | | 75 | | 73 |
| 10 | | | | | | 77 | | 76 |
| 11 | | | | | | 79 | | 79 |
| 12 | | | | | | 82 | | 81 |

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed:

1. A pharmaceutical composition in oral dosage form consisting essentially of a therapeutically effective amount of a medicament and a controlled release carrier, said carrier consisting essentially of a water insoluble polymer and a water insoluble inorganic salt, said polymer and inorganic salt interacting with said medicament to form a water insoluble barrier coating the medicament partially or completely to retard the release of the medicament from said pharmaceutical composition, said water insoluble polymer and said inorganic salt being present in an amount sufficient to read the release of the medicament in an aqueous medium, said polymer being present from about 1% up to about 50% by weight of the carrier, said inorganic salt being present in an amount of about 1% to about 95% by weight of the carrier, said carrier being present in an amount ranging by weight from about 1% to about 95% of the pharmaceutical composition, and said medicament being present in at least 5% by weight of the pharmaceutical composition.

2. The pharmaceutical composition according to claim 1 wherein the weight ratio of medicament to polymer is greater than about 3:1.

3. The pharmaceutical composition according to claim 2 wherein the weight ratio is at least about 5:1.

4. The pharmaceutical composition according to claim 1 wherein the weight ratio of inorganic salt to polymer ranges from about 1:1 to about 100:1.

5. The pharmaceutical composition according to claim 4 wherein the weight ratio ranges from about 1:1 to about 20:1.

6. The pharmaceutical composition according to claim 2 wherein the weight ratio of medicament to inorganic salt is greater than about 0.25:1.

7. The pharmaceutical composition according to claim 6 wherein the weight ratio is greater than 0.5:1.

8. The pharmaceutical composition according to claim 1 wherein the weight ratio of medicament to polymer is greater than about 3:1 and the weight ratio of medicament to inorganic salt is greater than about 0.25.

9. The pharmaceutical composition according to claim 8 wherein the weight ratio of medicament to inorganic salt is greater than about 0.5.

10. The pharmaceutical composition according to claim 8 wherein the weight ratio of medicament to polymer is at least about 5:1.

11. The pharmaceutical composition according to claim 1 wherein the water insoluble polymer is ethyl cellulose, cellulose acetate, polyvinyl acetate, esters of cellulose acetate, polyvinyl acrylate esters or acrylate polymer.

12. The pharmaceutical composition according to claim 11 wherein the insoluble polymer is an acrylate polymer.

13. The pharmaceutical composition according to claim 11 wherein the acrylate polymer is polymethyl methacrylate.

14. The pharmaceutical composition according to claim 1 wherein the inorganic salt is dicalcium phosphate, tricalcium phosphate, calcium carbonate, megnesium carbonate, or zinc carbonate.

15. The pharmaceutical composition according to claim 14 wherein the inorganic salt is dicalcium phosphate.

16. The pharmaceutical composition according to claim 5 wherein the weight ratio ranges from about 1:1 to about 5:1.

17. A pharmaceutical composition according to claim 1 wherein the water insoluble polymer is used in the form of an aqueous dispersion.

18. The pharmaceutical composition according to claim 1 wherein the water insoluble polymer is dissolved in an organic solvent.

19. The pharmaceutical composition according to claim 18 wherein the organic solvent is isopropyl alcohol or acetone or a combination of isopropyl alcohol and water or a combination of acetone and water.

20. The pharmaceutical composition according to claim 1 in the form of a tablet.

21. A pharmaceutical composition consisting essentially of a therapeutically effective amount of a medicament and a controlled release carrier, said carrier consisting essentially of methyl methacrylate polymer and a calcium inorganic salt which is insoluble in water at 25° C., said methyl methacrylate polymer and inorganic salt interacting with said medicament to form a water insoluble barrier coating the medicament partially or completely to retard the release of the medicament from said pharmaceutical composition, said methyl methacrylate polymer being present from about 1% up to about 50% by weight of the carrier, said calcium salt being present in amounts greater an 50% by weight of the carrier, said carrier being present from about 1% to about 95% of the pharmaceutical composition and the medicament being present in at least 5% by weight of the pharmaceutical composition.

22. The pharmaceutical composition according to claim 21 wherein the calcium salt is calcium carbonate, dicalcium phosphate, tricalcium phosphate or calcium sulfate.

23. The pharmaceutical composition according to claim 21 wherein the calcium salt is dicalcium phosphate.

24. The pharmaceutical composition according to claim 21 wherein the weight ratio of the calcium inorganic salt to methyl methacrylate polymer ranges from about 1:1 to about 100:1.

25. The pharmaceutical composition according to claim 24 wherein the weight ratio of the calcium inorganic salt to methyl methacrylate polymer ranges from about 1:1 to about 20:1.

26. The pharmaceutical composition according to claim 21 in the form of a tablet.

27. A pharmaceutical composition in oral dosage form consisting essentially of a therapeutically effective amount of a medicament and a controlled release carrier, said carrier consisting essentially of a water insoluble polymer, a water insoluble inorganic salt and at least a member selected from the group consisting of a lubricant and an excipient, said polymer and said inorganic salt interacting with said medicament to form a water insoluble barrier which coats the medicament partially or completely to retard the release of the medicament from said pharmaceutical composition, said polymer and said inorganic salt being present in an amount sufficient to retard the release of the medicament in an aqueous medium, said polymer being present from about 1% up to about 50% by weight of the carrier, said inorganic salt being present in an amount ranging from about 1% to about 95% by weight of the carrier, said carrier being present in an amount ranging from about 1% to about 95% by weight of the pharmaceutical composition, and said medicament being present in at least 5% by weight of the pharmaceutical composition.

28. The pharmaceutical composition according to claim 27 consisting essentially of the medicament, the water insoluble polymer, and the excipient.

29. The pharmaceutical composition according to claim 28 wherein the excipient is diethyl phthalate, triacetin, maltodextrin or triethyl citrate.

30. The pharmaceutical composition according to claim 28 wherein the excipient is a plasticizer, said plasticizer being present in amounts effective to increase the rate of release of the medicament.

31. The pharmaceutical composition according to claim 27 consisting essentially of said medicament, said inorganic salt, said water insoluble polymer and said lubricant.

32. A pharmaceutical composition in oral dosage form consisting essentially of a therapeutically effective amount of a medicament and a controlled release carrier, said carrier consisting essentially of a methyl methacrylate polymer, a calcium inorganic salt which is insoluble in water at 25° C. and at least a member selected form the group consisting of a lubricant and an excipient, said polymer and said inorganic salt interacting with said medicament to form a water insoluble barrier coating the medicament partially or completely to retard the release of the medicament from the pharmaceutical composition, said methyl methacrylate polymer being present from about 1% to about 50% by weight of the carrier, said calcium salt being present in amounts greater than about 50% by weight of the carrier, sad carrier being present from about 1% by weight to about 95% of the pharmaceutical composition and said medicament being present in at least 5% by weight of the pharmaceutical composition.

33. The pharmaceutical composition according to claim 32 consisting essentially of the medicament, the methyl methacrylate polymer, the water insoluble polymer and the excipient.

34. The pharmaceutical composition according to claim 33 wherein the excipient is a plasticizer which is present in amounts effective to increase the rate of release of the medicament.

35. The pharmaceutical composition according to claim 33 wherein the excipient is diethyl phthalate, triethylcitrate triacetin, or maltodextrin.

36. The pharmaceutical composition according to claim 35 wherein the excipient is diethyl phtalate.

37. A pharmaceutical composition in oral dosage form consisting essentially of a therapeutically effective amount of a medicament, a water insoluble polymer and an inorganic salt, sad inorganic salt and said water insoluble polymer interacting with said medicament to form a water insoluble barrier coating the medicament partially or wholly to retard the release of the medicament from said pharmaceutical composition, wherein the water insoluble polymer is present in an amount ranging from about 1% to about 20% of the pharmaceutical composition, the inorganic salt is present in an amount ranging from about 1% to about 94% by weight of the pharmaceutical composition and the medicament is present in at least 5% by weight of the pharmaceutical composition.

38. A pharmaceutical composition in oral dosage form consisting essentially of a therapeutically effective amount of a medicament, a water insoluble polymer, an inorganic salt and at least one member selected from the group consisting of an excipient and a lubricant said inorganic salt interacting with said water insoluble polymer to form a water insoluble barrier which coats the medicament partially or completely to retard the release of the medicament from the pharmaceutical composition, wherein the water insoluble polymer is present in an amount ranging from about 1% to about 20% of the pharmaceutical composition, the inorganic salt is present in an amount ranging from about 1% to about 94% by weight of the pharmaceutical composition, and the medicament is present in at least 5% by weight of the pharmaceutical composition.

* * * * *

UNITED STATES PATENT AND TRADEMARK OFFICE
CERTIFICATE OF CORRECTION

PATENT NO. : 6,437,000 B1
DATED : August 20, 2002
INVENTOR(S) : Nirmal Mulye

It is certified that error appears in the above-identified patent and that said Letters Patent is hereby corrected as shown below:

<u>Column 11,</u>
Line 60, "read" should read -- retard --

Signed and Sealed this

Fourth Day of November, 2003

JAMES E. ROGAN
*Director of the United States Patent and Trademark Office*